(12) United States Patent
Mediannikov et al.

(10) Patent No.: US 9,334,303 B2
(45) Date of Patent: May 10, 2016

(54) PEPTIDE COMPOUND USEFUL FOR INHIBITING AMYLOID PLAQUE FORMATION

(75) Inventors: Oleg Mediannikov, Marseilles (FR); Alexander Morozov, Moscou (RU)

(73) Assignee: KIMONELLA VENTURES LTD., Limassol (CY)

( * ) Notice: Subject to any disclaimer, the term of this patent is extended or adjusted under 35 U.S.C. 154(b) by 315 days.

(21) Appl. No.: 13/882,269

(22) PCT Filed: Oct. 24, 2011

(86) PCT No.: PCT/FR2011/052477
§ 371 (c)(1),
(2), (4) Date: Jun. 10, 2013

(87) PCT Pub. No.: WO2012/056157
PCT Pub. Date: May 3, 2012

(65) Prior Publication Data
US 2013/0252901 A1    Sep. 26, 2013

(30) Foreign Application Priority Data
Oct. 27, 2010  (FR) ..................... 10 58827

(51) Int. Cl.
| *C07K 5/10* | (2006.01) |
| *A61K 38/07* | (2006.01) |
| *C07K 5/11* | (2006.01) |
| *C07K 5/113* | (2006.01) |
| *C07K 5/117* | (2006.01) |

(52) U.S. Cl.
CPC . *C07K 5/10* (2013.01); *A61K 38/07* (2013.01); *C07K 5/1019* (2013.01); *C07K 5/1021* (2013.01); *C07K 5/1024* (2013.01); *Y02P 20/55* (2015.11)

(58) Field of Classification Search
CPC ........... A61K 38/07; C07K 5/10; C07K 5/126
See application file for complete search history.

(56) References Cited

U.S. PATENT DOCUMENTS

| 6,001,852 | A | 12/1999 | Gerolymatos | |
| 7,018,797 | B2 | 3/2006 | Reitz et al. | |
| 7,314,724 | B2 | 1/2008 | Castillo et al. | |
| 2004/0214165 | A1* | 10/2004 | Gicquel et al. | ................. 435/6 |
| 2005/0075493 | A1* | 4/2005 | Gaines | ................. 536/23.5 |

FOREIGN PATENT DOCUMENTS

| EP | 2130550 A1 | 12/2009 | |
| WO | 93/13789 | 7/1993 | |
| WO | WO/98/50078 | * 11/1998 | ............ A61K 47/48 |
| WO | 0196364 A2 | 12/2001 | |

OTHER PUBLICATIONS

Chu 1995 "Free solution identification of candidate peptides from combinatorial libraries by affinity capillary electrophoresis/mass spectrometry" J Am Chem Soc 117:5419-5420.*
Abelein 2015 "Zinc as a chaperone-mimicking agent for retardation of amyloid beta peptide fibril formation" PNAS 112(17):5407-12 (abstract only).*
Chu 1996 "Affinity capillary electrophoresis-mass spectrometry for screening combinatorial libraries" J Am Chem Soc 118:7827-7835.*
Kozin 2011 "Zinc-induced dimerization of the amyloid beta metal binding domain 1-16 is mediated by residues 11-14" Mol BioSyst 7:1053-1055.*
Chu, Y-H., et al. "Free solution identification of candidate peptides from combinatorial libraries by affinity capillary electrophoresis/mass spectrometry." Journal of the American Chemical Society, vol. 117, No. 19, May 17, 1995, pp. 5419-5420; which was cited in the International Search report mailed Jun. 2, 2012, corresponding to PCT/FR2011/052477.
Gomez-Ruiz, J. A., et al. "Sensory and Mass Spectrometric Analysis of the Peptidic Fraction Lower Than One Thousand Daltons in Manchego Cheese." American Dairy Science Organization, 2007. 90:4966-4973; which was cited in the International Search report mailed Jun. 2, 2012, corresponding to PCT/FR2011/052477.
International Search report mailed Jun. 2, 2012, corresponding to PCT/FR2011/052477.

* cited by examiner

*Primary Examiner* — Adam M Weidner
(74) *Attorney, Agent, or Firm* — Ladas & Parry LLP

(57) ABSTRACT

A peptide compound and composition useful for binding to amyloid-β peptides and/or preventing or reducing the formation of amyloid plaques, especially by inhibiting polymerization of the amyloid peptide in the form of amyloid plaques, and a method of treatment of a disease in which the formation of amyloid plaques occurs.

23 Claims, 5 Drawing Sheets

SEQUENCE LISTING

```
<160> NUMBER OF SEQ ID NOS: 68

<210> SEQ ID NO 1
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 1

His Ala Asp Asp
1

<210> SEQ ID NO 2
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 2

Asp Asp Ala His
1

<210> SEQ ID NO 3
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 3

Lys Ala Asp Asp
1
```

```
<210> SEQ ID NO 4
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 4

Asp Asp Ala Lys
1

<210> SEQ ID NO 5
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 5

Arg Ala Asp Asp
1

<210> SEQ ID NO 6
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 6

Asp Asp Ala Arg
1

<210> SEQ ID NO 7
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 7

His Ala Glu Asp
1

<210> SEQ ID NO 8
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 8

Asp Glu Ala His
1

<210> SEQ ID NO 9
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 9
```

```
Lys Ala Glu Asp
1

<210> SEQ ID NO 10
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 10

Asp Glu Ala Lys
1

<210> SEQ ID NO 11
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 11

Arg Ala Glu Asp
1

<210> SEQ ID NO 12
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 12

Asp Glu Ala Arg
1

<210> SEQ ID NO 13
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 13

His Ala Asp Glu
1

<210> SEQ ID NO 14
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 14

Glu Asp Ala His
1

<210> SEQ ID NO 15
<211> LENGTH: 4
<212> TYPE: PRT
<213> ORGANISM: artificial sequence
```

```
<220> FEATURE:
<223> OTHER INFORMATION: Tetrapeptide interacting with the 11-14 region
      of the beta amyloid

<400> SEQUENCE: 15

Lys Ala Asp Glu
1

<210> SEQ ID NO 16
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 16

Glu Asp Ala Lys
1

<210> SEQ ID NO 17
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 17

Arg Ala Asp Glu
1

<210> SEQ ID NO 18
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 18

Glu Asp Ala Arg
1

<210> SEQ ID NO 19
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 19

His Ala Glu Glu
1

<210> SEQ ID NO 20
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 20

Glu Glu Ala His
1
```

<210> SEQ ID NO 21
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 21

Lys Ala Glu Glu
1

<210> SEQ ID NO 22
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 22

Glu Glu Ala Lys
1

<210> SEQ ID NO 23
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 23

Arg Ala Glu Glu
1

<210> SEQ ID NO 24
<211> LENGTH: 4
<212> TYPE: PRT
<213> ORGANISM: artificial sequence
<220> FEATURE:
<223> OTHER INFORMATION: Tetrapeptide interacting with the 11-14 region
      of the beta amyloid

<400> SEQUENCE: 24

Glu Glu Ala Arg
1

<210> SEQ ID NO 25
<211> LENGTH: 16
<212> TYPE: PRT
<213> ORGANISM: artificial sequence
<220> FEATURE:
<223> OTHER INFORMATION: 1-16 region of the beta amyloid

<400> SEQUENCE: 25

Asp Ala Glu Phe Arg His Asp Ser Gly Tyr Glu Val His His Gln Lys
1               5                   10                  15

<210> SEQ ID NO 26
<211> LENGTH: 21
<212> TYPE: PRT
<213> ORGANISM: artificial sequence
<220> FEATURE:
<223> OTHER INFORMATION: Synthetic peptide fragment containing the 1-16
      region of the beta amyloid

<400> SEQUENCE: 26

```
Asp Ala Glu Phe Arg His Asp Ser Gly Tyr Glu Val His His Gln Lys
1               5                   10                  15

Gly Gly Gly Gly Cys
            20

<210> SEQ ID NO 27
<211> LENGTH: 4
<212> TYPE: PRT
<213> ORGANISM: artificial sequence
<220> FEATURE:
<223> OTHER INFORMATION: 13-16 region of the beta amyloid

<400> SEQUENCE: 27

His His Gln Lys
1

<210> SEQ ID NO 28
<211> LENGTH: 4
<212> TYPE: PRT
<213> ORGANISM: artificial sequence
<220> FEATURE:
<223> OTHER INFORMATION: 11-14 region of the beta amyloid

<400> SEQUENCE: 28

Glu Val His His
1

<210> SEQ ID NO 29
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 29

Ala Ala Glu Glu
1

<210> SEQ ID NO 30
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 30

His Ala Glu Ala
1

<210> SEQ ID NO 31
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 31

His Ala Ala Glu
1

<210> SEQ ID NO 32
<211> LENGTH: 4
<212> TYPE: PRT
```

```
<213> ORGANISM: artificial sequence
<220> FEATURE:
<223> OTHER INFORMATION: Tetrapeptide according to the invention
      modified with an alanine

<400> SEQUENCE: 32

Ala Ala Asp Asp
1

<210> SEQ ID NO 33
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 33

His Ala Ala Asp
1

<210> SEQ ID NO 34
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 34

His Ala Asp Ala
1

<210> SEQ ID NO 35
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 35

Ala Ala Asp Glu
1

<210> SEQ ID NO 36
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 36

Arg Ala Asp Ala
1

<210> SEQ ID NO 37
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 37

Arg Ala Ala Glu
1
```

```
<210> SEQ ID NO 38
<211> LENGTH: 4
<212> TYPE: PRT
<213> ORGANISM: artificial sequence
<220> FEATURE:
<223> OTHER INFORMATION: Tetrapeptide according to the invention
      modified with an alanine

<400> SEQUENCE: 38

Lys Ala Ala Glu
1

<210> SEQ ID NO 39
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 39

His Ala Glu Glu Ser Asp
1               5

<210> SEQ ID NO 40
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 40

His Ala Glu Glu Ala Asp
1               5

<210> SEQ ID NO 41
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 41

His Ala Glu Glu Ser Glu
1               5

<210> SEQ ID NO 42
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 42

His Ala Glu Glu Gly Glu
1               5

<210> SEQ ID NO 43
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids
```

-continued

```
<400> SEQUENCE: 43

His Ala Glu Glu Gln Glu
1               5

<210> SEQ ID NO 44
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 44

Leu Ala His Ala Glu Glu
1               5

<210> SEQ ID NO 45
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 45

Ile Ala His Ala Glu Glu
1               5

<210> SEQ ID NO 46
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 46

Phe Ser His Ala Glu Glu
1               5

<210> SEQ ID NO 47
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 47

Leu Gly His Ala Glu Glu
1               5

<210> SEQ ID NO 48
<211> LENGTH: 6
<212> TYPE: PRT
<213> ORGANISM: artificial sequence
<220> FEATURE:
<223> OTHER INFORMATION: Tetrapeptide SEQ. ID. NO.19 with 2 additional
      amino acids

<400> SEQUENCE: 48

Ile Ser His Ala Glu Glu
1               5

<210> SEQ ID NO 49
<211> LENGTH: 10
```

```
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 49

His Ser Leu Ala His Ala Glu Glu Ser Asp
1               5                   10

<210> SEQ ID NO 50
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 50

Lys Asn Ile Ala His Ala Glu Glu Ala Asp
1               5                   10

<210> SEQ ID NO 51
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 51

Arg Asn Phe Ser His Ala Glu Glu Ser Glu
1               5                   10

<210> SEQ ID NO 52
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 52

Lys Gln Leu Gly His Ala Glu Glu Gly Glu
1               5                   10

<210> SEQ ID NO 53
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 53

Arg Gln Ile Ser His Ala Glu Glu Gln Glu
1               5                   10

<210> SEQ ID NO 54
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 54

Asp Asp His Ser Leu Ala His Ala Glu Glu
```

-continued

```
<210> SEQ ID NO 55
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 55

Glu Glu Lys Asn Ile Ala His Ala Glu Glu
1               5                   10

<210> SEQ ID NO 56
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 56

Glu Glu Arg Asn Phe Ser His Ala Glu Glu
1               5                   10

<210> SEQ ID NO 57
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 57

Asp Glu Lys Gln Leu Gly His Ala Glu Glu
1               5                   10

<210> SEQ ID NO 58
<211> LENGTH: 10
<212> TYPE: PRT
<213> ORGANISM: artificial sequence
<220> FEATURE:
<223> OTHER INFORMATION: Tetrapeptide SEQ. ID. NO.19 with 6 additional
      amino acids

<400> SEQUENCE: 58

Asp Glu Arg Gln Ile Ser His Ala Glu Glu
1               5                   10

<210> SEQ ID NO 59
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 59

Ala Glu Glu
1

<210> SEQ ID NO 60
<211> LENGTH: 3
<212> TYPE: PRT
<213> ORGANISM: artificial sequence
<220> FEATURE:
<223> OTHER INFORMATION: Includes a portion of the tetrapeptide
``` according to SEQ. ID. NO.19

<400> SEQUENCE: 60

His Ala Glu
1

<210> SEQ ID NO 61
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 61

Ser His Ala
1

<210> SEQ ID NO 62
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 62

Gly His Ala
1

<210> SEQ ID NO 63
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 63

Glu Glu Gln
1

<210> SEQ ID NO 64
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 64

Ala His Ala
1

<210> SEQ ID NO 65
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 65

Ile Ala His
1

<210> SEQ ID NO 66

```
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 66

Phe Ser His
1

<210> SEQ ID NO 67
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 67

Glu Ser Asp
1

<210> SEQ ID NO 68
<211> LENGTH: 3
<212> TYPE: PRT
<213> ORGANISM: artificial sequence
<220> FEATURE:
<223> OTHER INFORMATION: Includes a portion of the tetrapeptide
      according to SEQ. ID. NO.19

<400> SEQUENCE: 68

Ile Ser His
1
```

PEPTIDE COMPOUND USEFUL FOR INHIBITING AMYLOID PLAQUE FORMATION

The present invention relates to a novel peptide compound especially useful for binding to amyloid-β peptides and/or preventing or reducing the formation of amyloid plaques, especially by inhibiting polymerization of said amyloid peptide in the form of amyloid plaques.

The present invention also relates to a use as a drug or for preparing or determining a drug with view to treating a neurodegenerative disease, especially Alzheimer's disease.

Alzheimer's disease is a neurodegenerative disease, especially of elderly persons, characterized by a long and irreversible decline in mental capacities, over a period of 5 to 15 years at the beginning of the disease, and, in subsequent stages of the disease, a loss of psychomotor functions.

Alzheimer's disease is one of the most frequent causes of dementia among elderly persons of more than 55 years old, regardless of gender or lifestyle [1].

For certain patients, the disease may be related to hereditary dysfunctions but, for the majority of the patients, the disease occurs sporadically without any identifiable reason [2].

To this day, no therapeutic method exists for treating sporadic or hereditary forms of the disease. It is now well known that Alzheimer's disease is not an inevitable consequence of the aging process but is induced by an abnormal phenomenon of aggregation of amyloid-β peptides (hereafter "Aβ") [3, 4].

Aβ is a peptide with 39 to 43 amino acids (SwissProt ID P05067) which forms after sequential cleavage of a protein precursor of the amyloid (designated hereafter as "APP"). The Aβ peptide is a compound which one commonly finds in biological fluids, such as blood or cerebrospinal liquid, in which it is present at low concentrations from 0.5 to 5 nM and this, identically in healthy individuals or in patients affected with Alzheimer's disease [5, 6].

On the other hand, progression of Alzheimer's disease is characterized by extracellular accumulation or deposit in the brain of the patient of so-called amyloid plaques. These plaques result from the conformation of the peptide Aβ monomer in the form of dimers and then of soluble oligomers of larger sizes, and then from their aggregation in the form of insoluble fibrillar β sheet aggregates, which finally give rise to amyloid plaques [7].

However, the exact molecular mechanism of the phenomenon of formation of amyloid plaques and of the triggering of Alzheimer's disease remains partly unexplained to this day.

Certain studies ascribe an intrinsically high amyloidogenic potential to fragments of the amino acids 17-42 of the COOH end of the Aβ peptide [9]. Other studies do not exclude that the fragments of the amino acids 1-16 of the Aβ peptide from the $NH_2$ end region of the Aβ peptide are involved in the pathogenesis of Alzheimer's disease [10].

To this day, with the whole of this available data, it may be considered that the 1-16 N-terminal region of the peptide Aβ is certainly the region involved in the most determining and conclusive way in the phenomenon of formation of amyloid plaques for the following reasons.

First of all, this region includes three mutations in rats, distinguishing the Aβ peptide of the rat from that of other mammals, even though rats are free of Alzheimer's disease.

The 1-16 N-terminal region was identified as the binding domain where zinc (Zn) and copper (Cu) are bound to the Aβ peptide [11-14]. Now, amyloid plaques are specifically characterized by abnormal high concentrations of divalent metals and in particular zinc [15]. Several studies and experiments, both in vivo and in vitro, show that high zinc concentrations induce the precipitation of the Aβ peptide, leading to the formation of amyloid plaques. Also, it was demonstrated that amyloid plaques more significantly form in the environment of neurones having high zinc concentrations [16-20].

This is why it is now considered that the blocking of the interaction of the Aβ peptide with zinc should lead to a decrease in the aggregation in the form of amyloid plaques of the peptide Aβ and thus prevent the pathologies associated therewith. Thus, in U.S. Pat. No. 6,001,852, as a drug for treating Alzheimer's disease, CLIOQUINOL is proposed, which is a zinc-chelating agent. However, the use of zinc-chelating agent requires specific targeting in the region of the binding domain where zinc binds to the Aβ peptide in order to avoid interference with normal homeostasis of zinc in the body.

Other studies [21-30] suggest that the receptors of nicotinic acetylcholine play a role as a main target of the neurotoxicity in connection with the failures of the cholinergic and cognitive system, induced by the formation of amyloid plaques. This is why in U.S. Pat. No. 7,018,797, a method was proposed for treating neurodegenerative diseases by inhibition of the binding of the amyloid-β peptides to the α-7 nicotinic acetylcholine receptor. In U.S. Pat. No. 7,018,797, compounds derived from naphthalene, in particular 5,8-dihydroxy-trans-2-di(N-propylamino)-3-methyl-1,2,3,4-tetrahydronaphthalene were more particularly proposed as compounds which may inhibit the binding of the Aβ peptide with said α-7 nicotinic acetylcholine receptor.

Other studies have shown an interaction of the region of the 13-15 amino acids of the Aβ peptide (HHQK, SEQ. ID. NO.27) with microglial cells of the brain by binding with heparan sulfate, which is a binding molecule of said cells, entering the category of glycosaminoglycans. The binding of the Aβ peptide on surface glycosaminoglycan molecules of microglial cells induces the formation of oligomers of Aβ peptides. The molecule Tramiprosate mimics glycosaminoglycans and inhibits the process of oligomerizaton of the Aβ peptides [31-36].

In U.S. Pat. No. 7,314,724, the use as a drug against Alzheimer's disease of soluble forms of laminins and its fragments (>10 Kda) which are capable of binding with Aβ and of keeping it in the monomeric state, has been proposed.

The more specific interaction mechanism between the Aβ peptides and the nicotinic acetylcholine receptors, as well as laminins, has not been explained.

The patent WO 93/13789 of SmithKline Beecham describes compounds with a complex formula including oligopeptides protected on both sides, the general formula of which covers two hexa- or hepta-peptides joined together through a chemical bond. The use of the compounds described in this document relates to the stimulation of the hemopoiesis in order to protect the body against infections, more particularly the stimulation of the myelopoietic system and does not explain the mode of action of said compounds.

US 2004/214165 describes the protein export system of mycobacteria. The sequence 646 of the 4 HAED amino acids is just a sequence of a terminal portion of one of the proteins of mycobacteria which participates in the protein export process. But, this HAED sequence is not described in US 2004/214165 as a formula of an individually isolated oligopeptide and even less a fortiori, as a therapeutically active peptide.

EP 2 130 550 describes a DEAH sequence (SEQ ID NO.39) as being a pattern of a helicase RNA protein, which has activity in the production of cytokines by mononuclear blood cells. But EP 2 130 550 does not describe a DEAH tetrapeptide as an isolated compound, and a fortiori, as a protected compound and, further a fortiori, as an active compound per se.

The article of Gomez-Ruiz et al. in J. Dairy Sci. 90:4966-4973 of 2007 describes the EDAK peptide and a product which is found in cheese stemming from the degradation of milk proteins caused by the fermentation by enzymes of lactobacilli or by enzymes which have been artificially added into the cheese. This article neither describes nor suggests that this isolated, purified, tetrapeptide and a fortiori protected by protecting groups, i.e. outside its mixture with cheese, may be a compound of interest taken separately or, a fortiori, may be an active compound per se.

The article of Chu et al. in J. Am. Chem. Soc. 1995, 117, 5419-54205 describes a method for identifying tetrapeptides by spectrometry. These tetrapeptides are identified as binding to a receptor, i.e. vancomycin, only the N-terminal end of the tetrapeptide being protected. DDAH tetrapeptide is just one of the peptides used in the experiment, selected for demonstrating the results of a manipulation. The article does not describe a particular activity of this DDAH tetrapeptide.

The object of the present invention is to provide a novel compound able to be used in determining or making a drug for treating or preventing diseases related to neurodegenerative disorders and/or to the formation of amyloid plaques by polymerization or aggregation of amyloid-β peptides.

More particularly, an object of the present invention is to provide a novel compound able to inhibit the interaction of amyloid-β peptide with Zn(II) ions. Indeed, it is known that the formation of amyloid plaques by aggregation or polymerization of amyloid-β peptides is induced by the formation of complexes of zinc with amyloid-β peptide, the zinc somewhat acting as a cofactor of this aggregation or polymerization.

More particularly, the object of the present invention is to provide a novel compound able to inhibit the formation of amyloid-β plaques and to allow treatment or prevention of Alzheimer's disease or any other degenerative disease related to the formation of amyloid plaques.

To do this, the present invention provides a peptide compound of the following general formula (I) or (II):

or

wherein, $R^1$ is an amino acid H, R or K residue;
$R^2$ is an amino acid A residue;
$R^3$ is an amino acid E or D residue;
$R^4$ is an amino acid E or D residue;
$R^a$ represents the N-terminal primary amine function of the amino acid $R^1$ or $R^4$, either free or substituted with a protected group, preferably an acetyl group (Ac),
$R^b$ represents the hydroxyl function of the C-terminal carboxyl group of the amino acid $R^1$ or $R^4$, either free or substituted with a protected group, preferably a group $NH_2$, NHR or NRR with R representing a $C_1$-$C_4$ alkyl chain, i.e. corresponding to a group of the amide type, preferably an amide group ($NH_2$).

It is understood that the peptide compounds according to the present invention are meant to be individually isolated and purified compounds, preferably with a purity degree of more than 98, preferably at least 99%, the remainder may be formed with other peptides inter alia.

In a known way and preferably, the amino acids $R^1$, $R^2$, $R^3$, $R^4$ will be configured in the form of their natural isomers L. But the amino acids $R^1$, $R^2$, $R^3$ and $R^4$, may also be analogs with a D configuration.

Still preferably, a peptide compound according to the present invention will have an L isomer purity degree of more than 98%, preferably at least 99% of L isomers.

The inventors have determined these tetrapeptides by defining the different amino acids according to a binding of the tetrapeptide with the EVHH site (SEQ. ID. NO.28) of the 11-14 region of the amyloid-β, while defining the amino acids $R^1$, $R^3$ and $R^4$, ionically of opposite sign, i.e. able to form strong ionic bonds with the amino acids E (glutamate) in position 11 for $R^1$ and respectively, H (histidine) in positions 13 and 14 for $R^3$ and respectively, $R^4$, i.e. 3 of the potentially involved sites in the binding of Zn(II) ions with the amyloid-β, and a hydrophobic amino acid A (alanine) able to form the strongest hydrophobic effect with V.

The thereby defined tetrapeptides form parallel (formula I) and antiparallel (formula II) non-covalent interactions with the EVHH target of the 11-14 region of the amyloid-β. Considering the fact that three of the four amino acids of the EBHH target region have strongly charged groups, amino acids were preferred, those having ionic complementarity for these three amino acids, while the selection of the amino acid $R^2$ was selected depending on the consideration of steric complementarity between the side chains of alanine and valine, even further stabilizing by hydrophobic contact between V and A, the ionic bonds with E and H.

The inventors have demonstrated experimentally that tetrapeptides, as defined above, binding to 3 Zn(II) ion chelating agents, namely the amino acids in positions 11, 13 and 14, represented an optimal compromise, by comparison with other relevant targets of different sizes comprising 1-4 Zn(II) chelating agents selected from the positions 6, 11, 13 and 14, notably from the regions 9-11, 10-12, 11-13, 12-14, 13-15, 14-16, 11-16, 5-14 and 9-14, and other definition criteria, notably in terms of peptide size, namely an optimal compromise of the possibility of using said compound in vivo for inhibiting the binding of the Zn(II) ions with the amyloid-β peptide, (Aβ) and the inhibition of oligomerization of the amyloid-β peptide, by binding of the tetrapeptide with the domain for binding Zn(II) ions to the amyloid-β peptide (Aβ).

It appears that the interaction force may be compromised by a bond at position 6. Conversely, a target only covering two sites in the positions 6 and 11 or 13 and 14 is insufficient for inhibiting the binding of the Zn(II) ions.

Another advantage of the tetrapeptides according to the invention is that they are strongly electrically charged which promotes the capability of passing through the blood-brain barrier.

The peptide compounds according to the invention therefore comprise, notably the sequences $R^1$—$R^2$—$R^3$—$R^4$ and $R^4$—$R^3$—$R^2$—$R^1$ of the explicit formulae I and II in Table 1, hereafter, and repeated in the sequences SEQ. ID. NOS.1 to 24 of the listing of sequences appended to the description.

TABLE 1

SEQ. ID. NO. 1 = HADD
SEQ. ID. NO. 2 = DDAH
SEQ. ID. NO. 3 = KADD
SEQ. ID. NO. 4 = DDAK
SEQ. ID. NO. 5 = RADD
SEQ. ID. NO. 6 = DDAR
SEQ. ID. NO. 7 = HAED
SEQ. ID. NO. 8 = DEAH
SEQ. ID. NO. 9 = KAED

TABLE 1-continued

SEQ. ID. NO. 10 = DEAK
SEQ. ID. NO. 11 = RAED
SEQ. ID. NO. 12 = DEAR
SEQ. ID. NO. 13 = HADE
SEQ. ID. NO. 14 = EDAH
SEQ. ID. NO. 15 = KADE
SEQ. ID. NO. 16 = EDAK
SEQ. ID. NO. 17 = RADE
SEQ. ID. NO. 18 = EDAR
SEQ. ID. NO. 19 = HAEE
SEQ. ID. NO. 20 = EEAH
SEQ. ID. NO. 21 = KAEE
SEQ. ID. NO. 22 = EEAK
SEQ. ID. NO. 23 = RAEE
SEQ. ID. NO. 24 = EEAR

The affinity of these tetrapeptides with a ligand corresponding to the fragment of the 1-16 region of the amyloid-β peptide was tested by calculating the dissociation constant Kd in Examples 1 to 3. Their dissociation constants are less than those of other tested peptides: tetrapeptides, tripeptides, hexapeptides or decapeptides not entering this definition by a factor $10^4$.

In a known way, said protective groups are groups compatible with pharmaceutical use in vivo. The function of the protective groups is to neutralize the electric charge of the amino and carboxyl ends of the peptide. More particularly, the N-terminal end may be protected with a formyl group (HCO—) or an acetyl group ($CH_3CO$—), and the C-terminal end may be protected by a group —$NH_2$, —NHR, —NRR, with R being a $C_1$-$C_4$ alkyl or further —O—R, with R being a $C_1$-$C_4$ alkyl or an alkylamine, such as —$OCH_3$, —$OCH_2CH_3$ or —$OCH_2CH_2NH_2$.

It is reminded that:
  the hydrophobic amino acids with an apolar group are alanine (A), valine (V), leucine (L), isoleucine (I), methionine (M), phenylalanine (F), proline (P), and tryptophan (W),
  the hydrophobic amino acids with a polar group are glycine (G), serine (S), threonine (T), cysteine (C), tyrosine (Y), asparagine (N) and glutamine (Q),
  the amino acids with a negatively charged group at neutral (acid) pH are aspartic acid (D) and glutamic acid (E), and
  the amino acids with a positive charged group at neutral (basic) pH are lysine (K), arginine (R) and histidine (H).

Natural α amino acids are all chiral, therefore optically active, except for glycine, and are all of the L configuration according to the FISHER configuration or S configuration according to the CAHN-INGOLD-PROLOG notation.

Three important types of interaction occur in bonds between peptides or secondary structures of peptides of the α helix or β folded sheet type resulting from the formation of hydrogen bridges between the CO and NH groups of the peptide backbone, i.e.:
  the hydrophobic effect: the amino acids, for which the radicals are hydrophobic, have more affinity for each other than for water molecules surrounding the protein. Conversely, hydrophilic amino acids tend to arrange themselves so as to be in contact with water,
  the ionic bonds: the radicals, which are positively charged, form ionic bonds with those which are negatively charged, and
  the hydrogen bonds which have interactions which are less strong than those resulting from ionic bonds and by the hydrophobic effect.

Preferably, the peptide compound according to the invention will be selected from the compounds of formula (I) or (II) wherein $R^1$—$R^2$—$R^3$—$R^4$ or respectively, $R^4$—$R^3$—$R^2$—$R^1$ represent HAEE, EDAR, EEAH, EEAK, EEAR, HADE, KADD, KAEE, RADD, RADE, RAEE, HADD, DDAK, KAED, DEAR or KADE. These peptides correspond in a different order to the sequences SEQ. ID. NOS.1, 3, 4, 5, 9, 12, 13, 15, 17, 18, 19, 20, 21, 22, 23 and 24.

The tetrapeptides above have a dissociation constant of their interaction with the fragment of the 1-16 region of the amyloid-β, Kd, as calculated in Examples 1-3 hereafter, lower than for the other tested peptides.

More preferably, the peptide compound according to the invention is from among the compounds of formula (I) or (II) wherein $R^1$—$R^2$—$R^3$—$R^4$ or $R^4$—$R^3$—$R^2$—$R^1$ represent one of the tetrapeptides: HADD, DDAK, RADD, KAED, DEAR, KADE, HAEE and RAEE. These peptides correspond to the sequences SEQ. ID. NOS.1, 4, 5, 9, 12, 15, 19 and 23, respectively. They have a still lower dissociation constant Kd than those of the other tested peptides, as calculated in Examples 1 to 3.

More preferably, the peptide compound according to the invention is selected from the compounds of formula (I) or (II), wherein $R^1$—$R^2$—$R^3$—$R^4$ or $R^4$—$R^3$—$R^2$—$R^1$ represent one of the two tetrapeptides HAEE and RADD.

$R^1$ is a residue of amino acid H,
$R^2$ is a residue of amino acid A;
$R^3$ is a residue of amino acid E,
$R^4$ is a residue of amino acid E.

The most preferred peptide compounds fit the formulas Ac-HAEE-$NH_2$ and Ac-RADD-$NH_2$.

The interaction dissociation constants Kd of both of these peptides with the ligand corresponding to a fragment of the 1-16 region of the amyloid-β, in Example 1 were the lowest of those of all the tested peptides.

Both of these peptide compounds also appear as being the most performing in terms of inhibition of the binding of Zn(II) ions to the amyloid-β 13 peptide and inhibition of polymerization or aggregation of the amyloid-β peptide in the form of a plaque, in the presence of physiological concentrations of Zn(II) ions, notably from 100 to 400 μM, by binding to said amyloid-β peptide, but, above all, both of these peptide compounds had properties for inhibiting the formation of amyloid plaques in an in vivo model on mice, the most performing ones as reported in the examples hereafter.

The object of the present invention is also the use of a peptide compound according to the invention, for reducing or preventing the binding of Zn(II) ions to the amyloid-β peptide by binding said peptide compound to said amyloid-β peptide.

Even more particularly, the object of the present invention is the use of a peptide compound according to the invention for reducing or preventing polymerization and/or aggregation of the amyloid-β peptide, in the presence of Zn(II) ions, more particularly at physiological concentrations of Zn(II) ions notably from 100 to 400 μM, by binding of said peptide compound to said amyloid-β peptide.

The present invention therefore provides the use of a peptide compound according to the invention, for treating a disease related to the formation of amyloid plaques.

The object of the present invention is also the use of a peptide compound according to the invention, as a drug, notably for treating a neurodegenerative disease and preferably for treatment of Alzheimer's disease.

The object of the present invention is also a useful composition in a use according to the invention, for which the active substance comprises at least one remainder R¹—R²—R³—R⁴ or R⁴—R³—R²—R¹ of a peptide compound according to the invention.

The active substance may be a multimer consisting of several monomers of sequence R¹—R²—R³—R⁴ or R⁴—R³—R²—R¹ bound through a bond capable of degrading in the body and thereby releasing the tetrapeptide, in a prolonged way over time, the active monomer.

In a known way, a peptide compound according to the invention may be formulated in the form of ester or physiologically acceptable salt derivatives.

More particularly, the object of the present invention is a pharmaceutical composition comprising a compound according to the invention or an active substance comprising at least one R¹—R²—R³—R⁴ or R⁴—R³—R²—R¹ residue of a peptide compound according to the invention with a pharmaceutically acceptable carrier, preferably via a parenteral, transcutaneous or transmucosal route.

More particularly, the pharmaceutical composition according to the invention will be formulated so as to be injectable, especially via an intravascular, intramuscular, subcutaneous, intraspinal or cerebrospinal route.

Other modes of administration via an oral, buccal, nasal, rectal or topical route may be contemplated provided that the peptide compound according to the invention is formulated in a form able to withstand degradation before attaining the target cells of the brain.

More preferably, said composition will appear in freeze-dried form.

More particularly, in a composition according to the present invention, the concentration of said peptide compounds is from 20 to 2,000 µM. The following examples describe and demonstrate the efficiency of the peptide compounds according to the invention, only given as an illustration and which should not be interpreted as a limitation of the present invention.

Other features and advantages of the present invention will become apparent in the light of the examples hereafter.

BRIEF DESCRIPTION OF THE DRAWINGS

FIG. 1 illustrates kinetic curves for the binding of the peptide Ac-HAEE-NH₂ with a ligand corresponding to the 1-16 region of amyloid-β at different concentrations, i.e. curve A=2 µM, curve B=5 µM, curve C=10 µM, curve D=15 µM, curve E=20 µM, curve F=25 µM and curve G=0 µM, with the equipment and according to the procedure of Example 1.

FIGS. 2 to 9 represent the kinetic curves for the binding of peptides of sequences SEQ. ID. NOS. 1, 4, 5, 9, 12, 15, 19 and 23 respectively with the equipment and according to the procedure of Example 3, said tetrapeptide being more purified than in Example 1.

Figure 1:
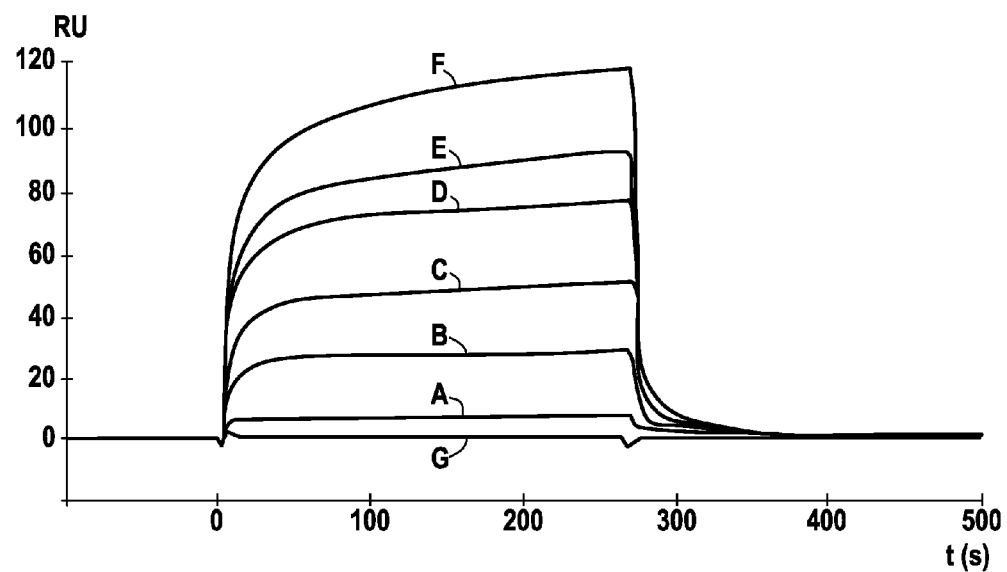
FIG. 1 shows kinetic curves for the binding of the peptide Ac-HAEE-NH₂ with a ligand corresponding to the 1-16 region of amyloid-β at different concentrations.
Figure 2:
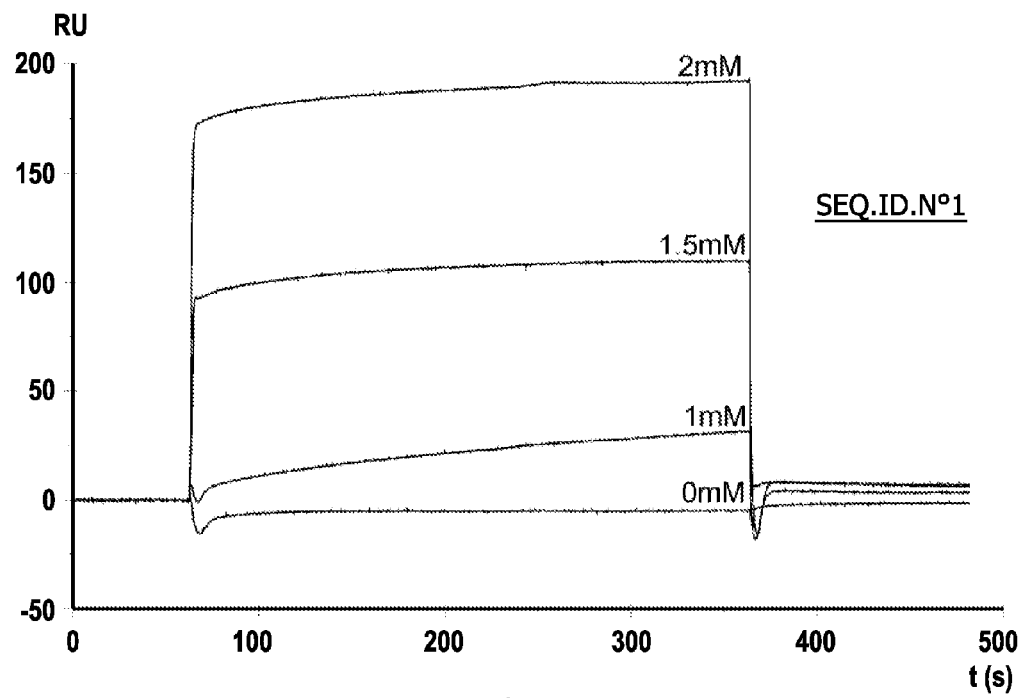
FIG. 2 shows kinetic curves for the binding of peptides of SEQ. ID. NO. 1.
Figure 3:
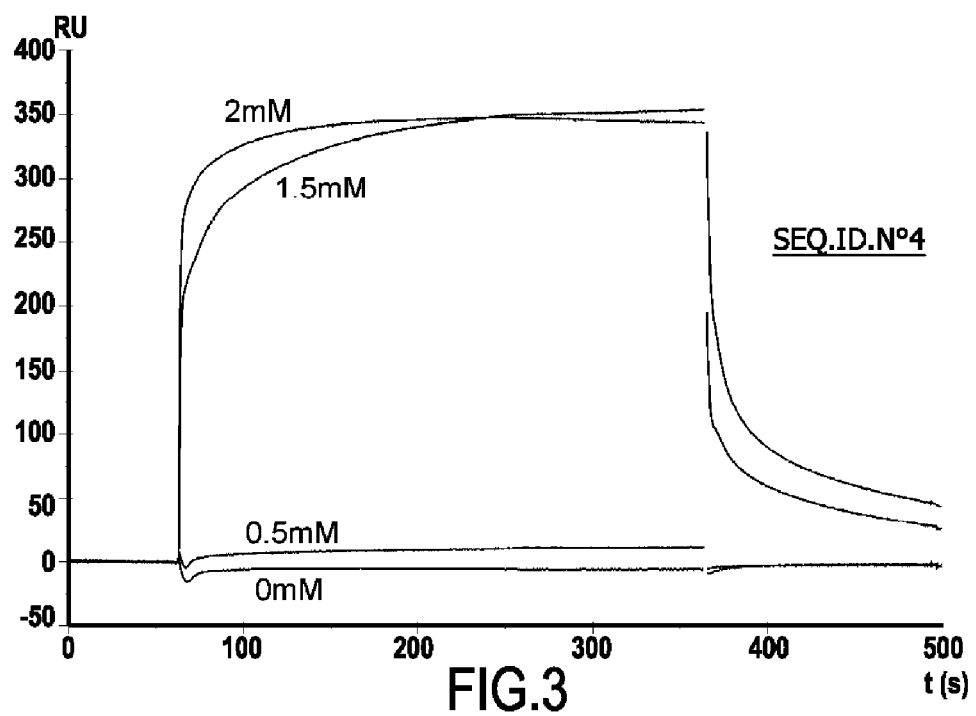
FIG. 3 shows kinetic curves for the binding of peptides of SEQ. ID. NO. 4.
Figure 4:
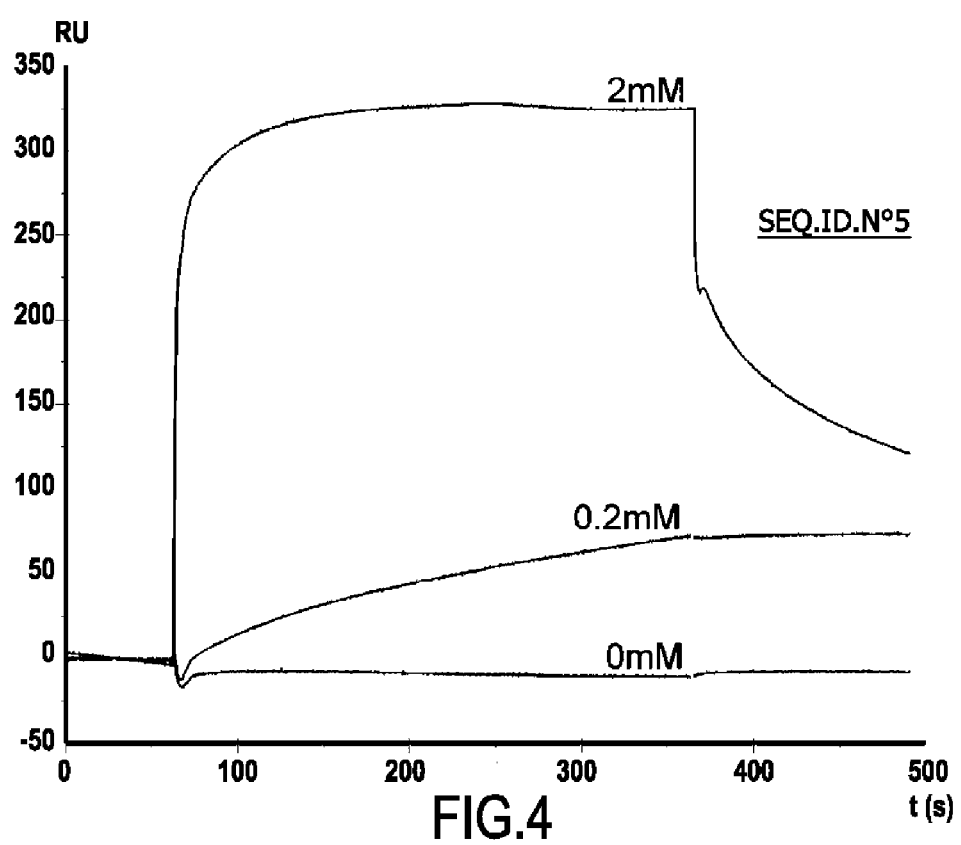
FIG. 4 shows kinetic curves for the binding of peptides of SEQ. ID. NO. 5.
Figure 5:
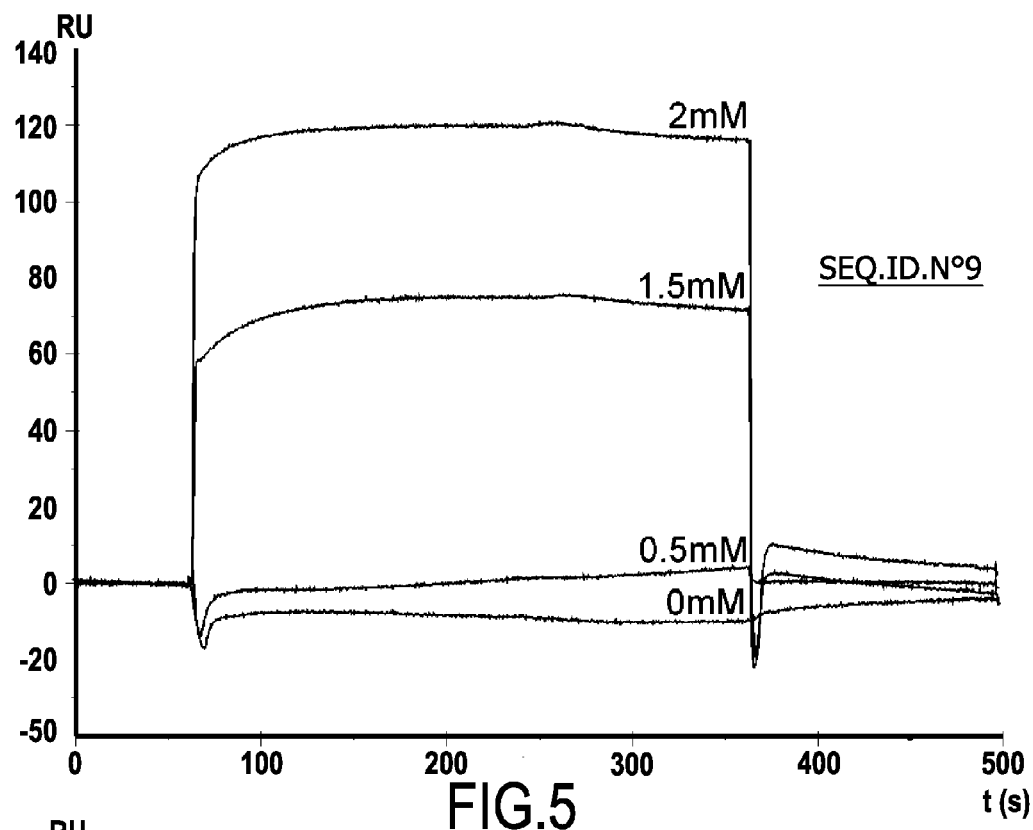
FIG. 5 shows kinetic curves for the binding of peptides of SEQ. ID. NO. 9.
Figure 6:
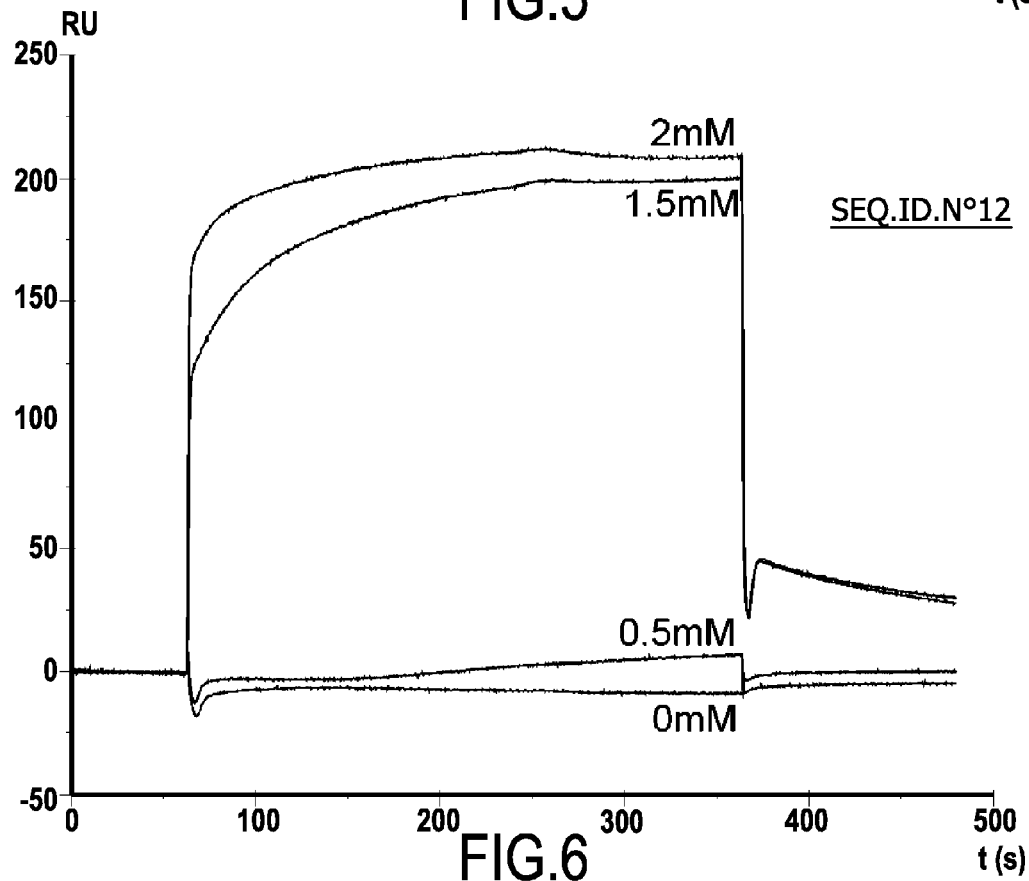
FIG. 6 shows kinetic curves for the binding of peptides of SEQ. ID. NO. 12.
Figure 7:
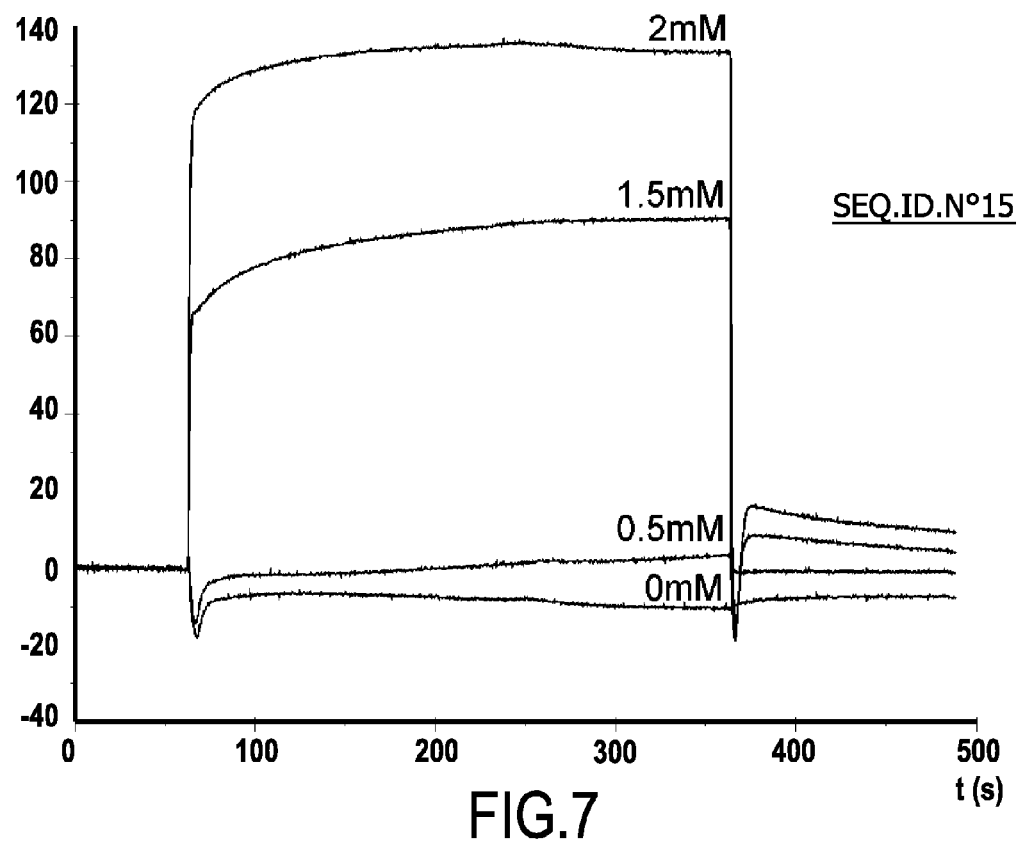
FIG. 7 shows kinetic curves for the binding of peptides of SEQ. ID. NO. 15.
Figure 8:
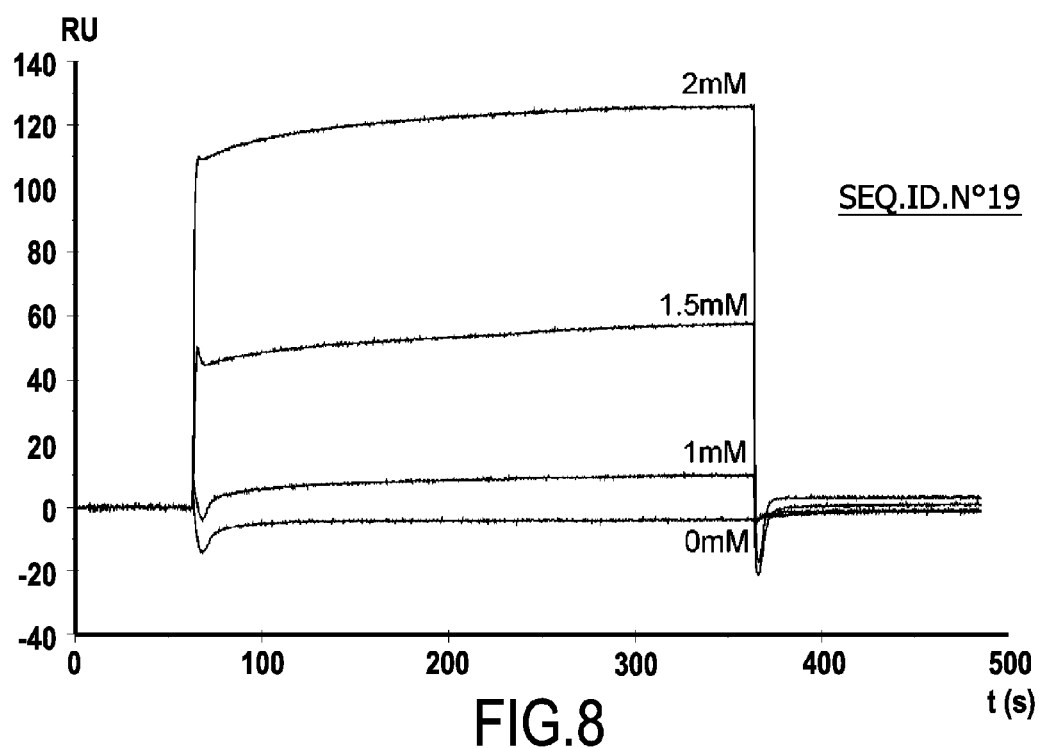
FIG. 8 shows kinetic curves for the binding of peptides of SEQ. ID. NO. 19.
Figure 9:
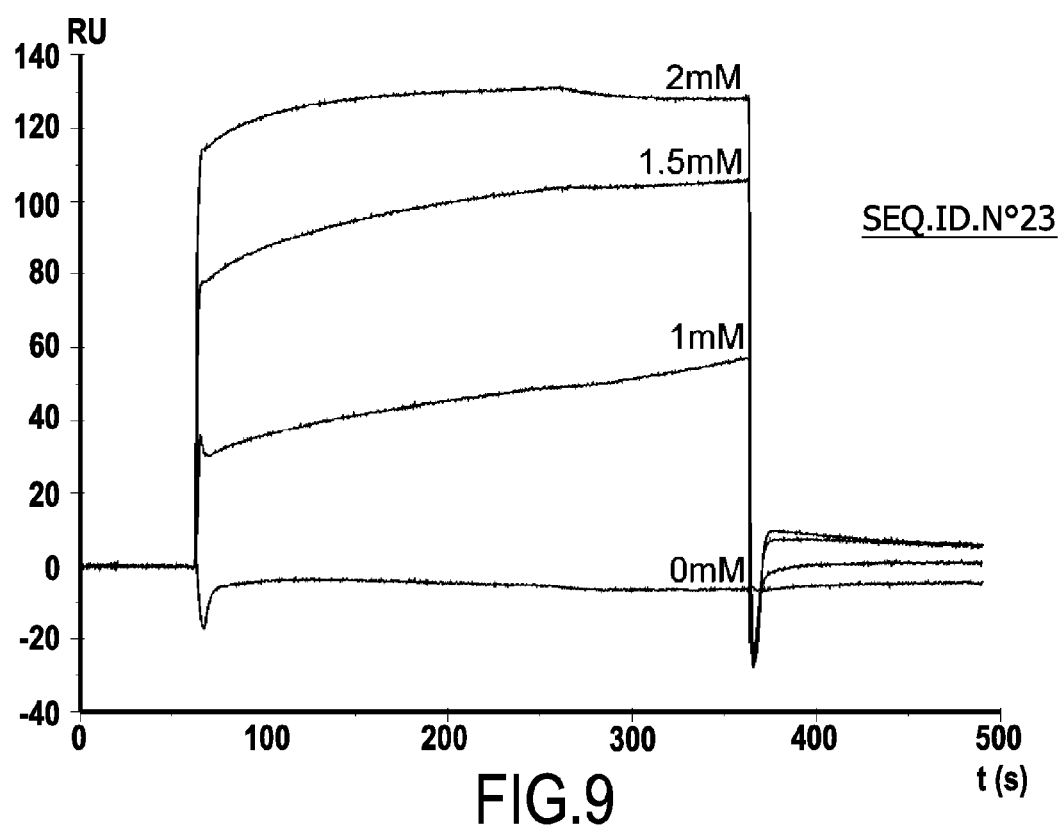
FIG. 9 shows kinetic curves for the binding of peptides of SEQ. ID. NO. 23.

The variation of the response unit of the spectrometer in ordinates (RU=Response unit) over time gives the possibility of calculating the dissociation constant Kd of the bond of the tetrapeptide with the fragment of the region 1-16 of the amyloid-β peptide, as reported in Examples 1 and 3.

EXAMPLE 1

Binding of the Tetrapeptide Ac-HAEE-NH₂ (SEQ. ID. NO.19) to an Immobilized Peptide Fragment Corresponding to the 1-16 Region of the Amyloid-β Peptide An analysis was performed by surface plasmon resonance (SPR) spectroscopy of the bond of the tetrapeptide Ac-HAEE-NH₂ to an immobilized peptide fragment corresponding to the region 1-16 of the amyloid-β peptide.

With this analysis, it is possible to calculate the dissociation constant Kd of the interaction of the peptide with the immobilized ligand, it being understood that the value of Kd is all the more smaller since the interaction with the ligand and therefore the stability of the formed interaction complex are high. In these methods, it is considered that a significant specific interaction is present if Kd is less than or equal to $10^{-4}$ M. On the other hand if Kd is greater than or equal to $10^{-3}$ M, it is considered that there is no significant binding or interaction.

Surface plasmon resonance is a physical phenomenon, mainly known for its use as a method for measuring the bond of a ligand on a receptor adsorbed at the surface of a metal layer. An SPR detection system measures the variation of the refractive index in the vicinity of the interface when the ligand binds to the receptor.

The principles of surface plasmon resonance spectroscopy are described in Nagata, K., and Handa, H. (eds), Springer-Verlag, Tokyo, 2000.

More specifically, in an SPR spectroscopy system, for example applying a biosensor from BIACORE, after immobilization of the ligand at the surface of a sensor of the chip type, in this case here the amyloid-β fragment, the analyte reagent is injected on said surface at a constant flow rate through systems of microfluidic channels. Polarized light emitted by a light source is reflected on the gold-covered surface of the chip, and then detected by a diode reader. According to the binding of the ligand and of the analyte molecule, the intensity of the reflected light is different. The variation in the response of the spectrometer (RU=Response unit) allows calculation of the dissociation constant of the interaction.

The chips of the biosensor came from GE Healthcare (USA). The SPR spectroscopy experiments were conducted with the BIACORE 3000 apparatus. The reagents for immobilizing the amyloid-β peptide fragment (EDC, NHS, PDEA and cysteine) were bought from GE Healthcare (USA). The buffer used for immobilizing the peptide ligand by formation of thiol bonds was 10 mM sodium acetate at pH 4.5. The regeneration buffer was an HBS buffer containing a medium with 10 mM HEPES and 3 mM EDTA, 0.005% of surfactant P20 and 150 mM NaCl at pH 7.4. The immobilization buffer was a HBS buffer at pH 7.4 and a HEPES buffer at pH 6.8, 50 mM, with 100 µM of Zn(II) ions for the reactive tetrapeptide Ac-HAEE-NH₂. All the buffers were filtered before use.

The peptide fragment of the ligand was: Ac-DAEFRHDS-GYEVHHQKGGGGC-NH$_2$, corresponding to the sequence SEQ. ID. NO.26. This peptide with 21 amino acids contains the 16 amino acids of the N-terminal end of the binding domain of the amyloid-β, i.e. DAEFRHDSGYEVHHQK (SEQ. ID. NO.25), followed by 4 glycine amino acids and a cysteine C-Terminal end. Cysteine is necessary for immobilizing the ligand on the surface of the chip through a thiol bond according to the procedure of the supplier. 4 glycine amino acids therefore form a binding tetrapeptide ("linker") between the chip and the ligand. Further, the thereby immobilized ligand has enough flexibility relatively to the surface, so as to validly mimic the interaction conditions between the tetrapeptide reagent and the ligand. This ligand was bound onto a CM5 chip of the biosensor, by following the standard procedure through a thiol bond under conditions described in the handbook of the sensor provided by the supplier GE Healthcare (USA).

The flow rate applied in all the steps was 5 μl/min. The carboxymethyl dextran matrix was activated by injecting a 1:1 mixture of 1-ethyl-3(3-dimethylaminopropyl)-carbodiimide (EDC) and of N-hydroxysuccinimide (NHS), i.e. 30 μl of EDC at 400 mM and NHS at 100 mM, followed by an injection of 80 mM PDEA (2-(2-pyridinyldithio)-ethaneamine) in solution in 0.1 M sodium borate at a pH of 8.5. The peptide ligand in solution in a sodium acetate buffer in an amount of 0.05 mg/ml was then injected. The thiol groups having not reacted at the surface of the CM5 chips, were removed with a 50 mM cysteine solution in a 0.1 M sodium acetate buffer at pH 4, in order to provide a surface which gave a response unit variation (RU) of about 700 arbitrary units with a control liquid sample. The control liquid was reacted with the surface of the chip according to the same procedure.

The reagent Ac-HAEE-NH$_2$ was prepared by dilution with 7 concentrations, i.e. 0, 2, 5, 10, 15, 20 and 25 μM, and injected in a multichannel mode (20 μL QUICKINJECT, 5 μL/min). The surface of the chip was exposed for 330 seconds to the reagent buffer solution in order to track its binding. The surface of the chip was then regenerated by injecting a regeneration buffer (20 μL). The data of the control lane were subtracted from raw data of the lane corresponding to the immobilized reagent peptides. Next, the dissociation constant Kd was calculated in a known way from curves established for the response at equilibrium (Req) versus the concentration (M) in the BIA evaluation 4.1 program. 7 reagent samples at different concentrations were therefore injected into channels with the ligand immobilized on the surfaces of the chip.

The kinetic binding curves of Ac-HAEE-NH$_2$ to the immobilized peptides, after subtraction of the responses of the control, are reported in FIG. 1.

The curves of FIG. 1 gave the possibility of calculating the dissociation constant Kd of the interactions, which was evaluated to be $2.2 \times 10^{-8}$ M.

In the presence of physiological concentrations of Zn(II) ions (100-400 μM), the dissociation constant was practically unchanged. However, high concentrations of Zn(II) ions (10 mM) suppressed the interactions of the ligand with the reagent. If it is considered that the bindings of Zn(II) ions to the Aβ peptides are characterized by micromolar (μM) values of Kd, it may be estimated that the reagent Ac-HAEE-NH$_2$ is in competition with the Zn(II) ions for binding onto the Aβ peptide. However, the affinity of the reagent with the Aβ peptide is much higher than that of Zn(II) ions, so that the peptide Ac-HAEE-NH$_2$ prevents the binding of Zn(II) ions at physiological concentrations with the peptide Aβ.

More specifically, the affinity of the Ac-HAEE-NH$_2$ reagent with the Aβ amyloid is greater than that of the Zn(II) ions.

The experiments have demonstrated that in the presence of physiological concentrations of Zn(II) ions at micromolar levels (less than 500 μM), the binding of HAEE to the 1-16 domain of the amyloid-β is practically not altered in the presence or in the absence of Zn(II) ions. On the other hand, higher concentrations of Zn(II) ions, of the order of 1 millimolar (mM), suppress the interactions between HAEE and the 1-16 domain of Aβ. These data indicate that HAEE has greater affinity for the target domain than the Zn(II) ions, and is capable of blocking the interaction between the Zn(II) ions and Aβ when the Zn(II) ions are at physiological concentrations.

EXAMPLE 2

Comparative Example

The experiments for binding to a target peptide ligand corresponding to the 1-16 region of the amyloid-β were conducted according to the procedure described in Example 1 with other peptides described hereafter.

1—All the 23 other tetrapeptides listed in Table 1 above, corresponding to the sequences SEQ. ID. NOS.1 to 18 and 20 to 24 with the same protective groups $R^a$=Ac and $R^b$=NH$_2$, were tested and their dissociation constants Kd were from $10^{-5}$ to $10^{-6}$ M. These dissociation constants were practically unchanged in the presence of zinc physiological concentrations from 100 to 400 μM. The tetrapeptides according to the invention, having the lowest dissociation constant Kd (except for HAEE), were: EDAR, EEAH, EEAK, EEAR, HADE, KADD, KAEE, RADD, RADE, RAEE, HADD, DDAK, KAED, DEAR and KADE.

These values correspond to strong bonds with the target ligand of the 1-16 region of the amyloid-βpeptide.

2—Other comparative examples with 10 different tetrapeptides, analogous to tetrapeptides from Table 1 but wherein one amino acid was replaced with alanine (A), i.e. said following tetrapeptides: A<u>AEE</u>, H<u>A</u>EA, HA<u>AE</u>, A<u>ADD</u>, HA<u>AD</u>, H<u>ADA</u>, A<u>ADE</u>, R<u>ADA</u>, R<u>AAE</u>, K<u>AAE</u>, corresponding to these sequences SEQ. ID. NOS. 29 to 38, respectively, had a significantly greater dissociation constant, i.e. Kd from $10^{-3}$ to $10^{-4}$ M, corresponding to a non-specific or non-significant interaction with the target ligand.

SEQ. ID. NO.29 is drawn from SEQ. ID. NO.23, wherein the first amino acid R was replaced with A.

SEQ. ID. NO.30 is drawn from SEQ. ID. NO.19, wherein the last amino acid E was replaced with A.

SEQ. ID. NO.31 is drawn from SEQ. ID. NO.19, wherein the third amino acid E was replaced with A.

SEQ. ID. NO.32 is drawn from SEQ. ID. NO.5, wherein the first amino acid R was replaced with A.

SEQ. ID. NO.33 is drawn from SEQ. ID. NO.7, wherein the third amino acid E was replaced with A.

SEQ. ID. NO.34 is drawn from SEQ. ID. NO.1, wherein the last amino acid D was replaced with A.

SEQ. ID. NO.35 is drawn from SEQ. ID. NO.13, wherein the first amino acid H was replaced with A.

SEQ. ID. NO.36 is drawn from SEQ. ID. NO.5, wherein the last amino acid D was replaced with A.

SEQ. ID. NO.37 is drawn from SEQ. ID. NO.23, wherein the third amino acid E was replaced with A.

SEQ. ID. NO.38 is drawn from SEQ. ID. NO.21, wherein the third amino acid E was replaced with A.

3—10 different tripeptides corresponding to the tetrapeptide of SEQ. ID. NO.19 (HAEE) were tested, wherein 1, 2 or 3 amino acids according to the following sequences SEQ. ID. NOS. 59 to 68: AEE, HAE, SHA, GHA, EEQ, AHA, IAH, FSH, ESD, ISH were removed. It will be noted that the tripeptide AEE corresponds to a complementary tripeptide of the 12-14 region according to the complementarity criteria explained earlier. These tripeptides were complementary to the regions of the Aβ peptides, 9-11, 10-12, 11-13, 12-14, 13-15 and 14-16.

These 10 different tripeptides also had a dissociation constant from $10^{-3}$ to $10^{-4}$ M, reflecting a lack of significant or specific interaction with the target.

4—Further, 10 different hexapeptides, including the tetrapeptide SEQ. ID. NO.19 (HAEE), preferred according to the invention, added with 2 amino acids at its N-terminal end or at its C-terminal end were tested, namely the following hexapeptides: HAEESD, HAEEAD, HAEESE, HAEEGE, HAEEQE, LAHAEE, IAHAEE, FSHAEE, LGHAEE, ISHAEE. These hexapeptides were complementary to the regions of the Aβ peptide 11-16 and 9-14.

These 10 hexapeptides, repeated in the listing of sequences in sequences SEQ. ID. NOS. 39 to 48, also had a relatively high dissociation constant Kd from $10^{-3}$ to $10^{-4}$ M, reflecting a lack of significant or specific interaction with the ligand of the 1-16 region of the amyloid-β.

These 10 hexapeptides all corresponded to sequences for which the 2 additional amino acids might interact with the amino acids 15-16 (QK) of the amyloid-β for the N-terminal extensions and with the amino acids GY of the regions 9-10 (GY) of the amyloid-β, in accordance with the ionic or hydrophobic interactions as explained earlier.

5—Finally, 10 decapeptides taken from the listing of sequences in the following sequences SEQ. ID. NO.49 to 58 were tested: HSLAHAEESD, KNIAHAEEAD, RNFSHAEESE, KQLGHAEEGE, RQISHAEEQE, DDHSLAHAEE, EEKNIAHAEE, EERNFSHAEE, DEKQLGHAEE, DERQISHAEE, which has a dissociation constant Kd from $10^{-3}$ to $10^{-4}$ M, reflecting a lack of significant or specific interaction with the target.

These decapeptides again took a preferred tetrapeptide according to the invention, SEQ. ID. NO.19 (HAEE), with 2 additional amino acids at the N-terminal end and 4 additional amino acids at the C-terminal end for SEQ. ID. NOS. 49 to 53 and 6 additional amino acids for the decapeptides SEQ. ID. NOS. 54 to 58. The decapeptides SEQ. ID. NOS.49 to 58 all comprised additional amino acids defined as being capable of interacting with the amino acids of the regions 7-10 and 15-16 of the amyloid-β for SEQ. ID. NOS.49 to 53, and of the region 5-10 of the amyloid-β for SEQ. ID. NOS.54 to 58, which targeted the region 5-14 of the Aβ peptide.

All the peptides tested above in sections 1— and 5— included a protective group of the N-terminal amine function, $R^a$=Ac and a protective group of the hydroxyl function of the C-terminal carboxyl group, $R^b$=NH$_2$.

EXAMPLE 3

Binding of the Tetrapeptides According to the Invention to an Immobilized Peptide Fragment Corresponding to the Region 1-16 of the Amyloid-β Peptide The binding tests described in Example 1 were reproduced, with the same materials, reactives and procedures except for the following significant differences:

the BIACORE apparatus applied was the BIACORE T100 apparatus. This BIACORE T100 apparatus produces more accurate results than the BIACORE 3000 because it includes a degasification system upon injecting the analyte on the sensor and because the method for detecting immobilized ligand/analyte intermolecular complexes on the CM5 chip is more accurate.

the tetrapeptides according to the invention used were purified to at least 99% in L isomers according to HPLC data, the D isomers were prevented from forming and/or removed during the synthesis. In Example 1, the tetrapeptides only included 98% of L isomers.

the concentrations of the tetrapeptides according to the invention applied were 50; 100; 200; 500; 1,000; 1,500 and 2,000 μM.

these experiments were conducted in the absence of zinc.

the surface of the CM5 chips provided a surface which gave a variation of response units (RU) of about 1,023 arbitrary units, with a control liquid sample.

The curves of the kinetics of FIGS. 2 to 9, allow calculation of the dissociation constant Kd according to the method described in the prior publications (notably see reference [39]), i.e. that the curves allow calculation of the kon and koff constant with the formula:

$$dR/dt = k_{on}C(Rmax-R) - k_{off}R, \text{ wherein:}$$

R represents the response in ordinates
C represents the concentration of the analyte
Rmax the theoretical maximum value of R,
the dissociation constant Kd being given by the formula Kd=koff/kon.

In Table 2, the values of the dissociation Kd calculated for the tetrapeptides of the sequences SEQ. ID. NOS.1, 4, 5, 9, 12, 15, 19 and 23, which have the lowest values, are reported.

TABLE 2

| Analyte | Kd × 10$^4$M | k$_{on}$ × M$^{-1}$s$^{-1}$ | k$_{off}$ × 10$^{-3}$ s$^{-1}$ |
|---|---|---|---|
| SEQ. ID. NO. 1 | 32.5 ± 0.9 | 3.20 ± 0.08 | 10.40 ± 0.02 |
| SEQ. ID. NO. 4 | 13.7 ± 0.5 | 4.57 ± 0.09 | 6.2 ± 0.1 |
| SEQ. ID. NO. 5 | 0.13 ± 0.02 | 18.5 ± 0.1 e1 | 0.24 ± 0.04 |
| SEQ. ID. NO. 9 | 33 ± 7 | 5.7 ± 0.9 | 19 ± 1 |
| SEQ. ID. NO. 12 | 19.8 ± 0.7 | 3.58 ± 0.08 | 7.09 ± 0.09 |
| SEQ. ID. NO. 15 | 45 ± 3 | 2.2 ± 0.1 | 9.6 ± 0.2 |
| SEQ. ID. NO. 19 | 0.9 ± 0.3 | 0.37 ± 0.05 | 0.035 ± 0.008 |
| SEQ. ID. NO. 23 | 77 ± 6 | 1.5 ± 0.1 | 11.20 ± 0.08 |

In this case the two analytes comprising the sequences SEQ. ID. NOS.5 and 19 had the lowest dissociation constants Kd, comprised between about $10^{-4}$ and $10^{-5}$ M.

The other six tetrapeptides of the sequences SEQ. ID. NOS. 4, 9, 12, 15 and 23 gave Kd values comprised between $10^{-3}$ and $10^{-2}$ M.

The other tetrapeptides according to this model showed dissociation constants Kd of more than $10^{-2}$ M.

EXAMPLE 4

Inhibition of the Formation of Amyloid-β Plaques by Polymerization or Aggregation The aggregation phenomenon of Aβ peptides in the form of amyloid plaques was demonstrated in vitro by using the "SYNTHALOID SCREENING PLATE®" kit from QUALITY CONTROLLED BIOCHEMICALS Inc. USA, involving the application of plaques covered with crystallization centers of the Aβ peptide and Aβ peptides marked with a fluorescent marker with the purpose of detecting aggregates (37, 38).

The complete β peptide 1-40 was used, marked by a fluorescent marker in a buffer containing 50 mM HEPES medium, pH 7.4, 0.1% BSA and 10% FCS, this buffer intrinsically containing physiological concentrations of Zn(II) ions, and inhibitors of proteases. Said plates were in the form of plates including 96 wells, into which 100 µL of marked Aβ peptides (1-40) at a concentration of 100 nM were poured. They were left to incubate for 3 hours at room temperature in the wells.

In certain wells, tetrapeptides AC-HAEE-NH$_2$ and Ac-RADD-NH$_2$ according to the invention, were introduced at different concentrations depending on the wells (0, 5, 10, 20, 40, 80, 100 and 150 µM), for checking the effect of tetrapeptides according to the invention on the aggregation phenomenon of Aβ peptides.

To do this, at the end of the incubation, the unbound proteins in the wells were removed with three washings, by using the buffer solution above. The amount of bound proteins in the form of aggregates, bound to the well, was measured by measuring the fluorescence intensity.

The tetrapeptides HAEE and RADD according to invention actually inhibit the aggregation of the Aβ peptide with inhibitory concentrations $IC_{50}$ of 20 µM. It is recalled that the concentration $IC_{50}$ represents the concentration with which aggregation of 50% of the Aβ peptide introduced into the well may be prevented.

According to a test described in the user manual of the kit of "SYNTHALOID SCREENING PLATE®" plates, it is considered that a compound that inhibits the binding of a protein on a solid support, if its $IC_{50}$ concentration is less than 100 µM.

Studies over time show that prolonged incubation for at least 1 hour of the amyloid aggregates with the HAEE and RADD tetrapeptides at concentrations of 20, 40, 80, 100 and 150 µM further cause irreversible disaggregation of the amyloid aggregates.

BIBLIOGRAPHIC REFERENCES

[1] Cummings, J. L. (2004). Alzheimer's disease. N Engl J Med 351, 56-67.
[2] Selkoe, D. J. (2001). Alzheimer's disease: genes, proteins, and therapy. Physiol Rev 81, 741-66.
[3] Glenner, G. G. and Wong, C. W. (1984). Alzheimer's disease and Down's syndrome: sharing of a unique cerebrovascular amyloid fibril protein. Biochem Biophys Res Commun 122, 1131-5.
[4] Masters, C. L., Simms, G., Weinman, N. A., Multhaup, G., McDonald, B. L. and Beyreuther, K. (1985). Amyloid plaque core protein in Alzheimer disease and Down syndrome. Proc Natl Acad Sci USA 82, 4245-9.
[5] Mayeux, R. et al. (1999). Plasma amyloid beta-peptide 1-42 and incipient Alzheimer's disease. Ann Neurol 46, 412-6.
[6] Seubert, P. et al. (1992). Isolation and quantification of soluble Alzheimer's beta-peptide from biological fluids. Nature 359, 325-7.
[7] Hardy, J. and Selkoe, D. J. (2002). The amyloid hypothesis of Alzheimer's disease: progress and problems on the road to therapeutics. Science 297, 353-6.
[8] Luhrs, T., Ritter, C., Adrian, M., Riek-Loher, D., Bohrmann, B., Dobeli, H., Schubert, D. and Riek, R. (2005). 3D structure of Alzheimer's amyloid-beta (1-42) fibrils. Proc Natl Acad Sci USA 102, 17342-7.
[9] Gowing, E., Roher, A. E., Woods, A. S., Cotter, R. J., Chaney, M., Little, S. P. and Ball, M. J. (1994). Chemical characterization of A beta 17-42 peptide, a component of diffuse amyloid deposits of Alzheimer disease. J Biol Chem 269, 10987-90.
[10] Mattson, M. P. (1995). Untangling the pathophysiochemistry of beta-amyloid. Nat Struct Biol 2, 926-8.
[11] Guilloreau, L., Damian, L., Coppel, Y., Mazarguil, H., Winterhalter, M. and Faller, P. (2006). Structural and thermo dynamical properties of CuII amyloid-beta16/28 complexes associated with Alzheimer's disease. J Biol Inorg Chem 11, 1024-38.
[12] Kozin, S. A., Zirah, S., Rebuffat, S., Hoa, G. H. and Debey, P. (2001). Zinc binding to Alzheimer's Abeta(1-16) peptide results in stable soluble complex. Biochem Biophys Res Commun 285, 959-64.
[13] Mekmouche, Y., Coppel, Y., Hochgrafe, K., Guilloreau, L., Talmard, C., Mazarguil, H. and Faller, P. (2005). Characterization of the ZnII binding to the peptide amyloid-beta1-16 linked to Alzheimer's disease. Chembiochem 6, 1663-71.
[14] Zirah, S. et al. (2004). Zinc binding agonist effect on the recognition of the beta-amyloid (4-10) epitope by anti-beta-amyloid antibodies. Biochem Biophys Res Commun 321, 324-8.
[15] Lovell, M. A., Robertson, J. D., Teesdale, W. J., Campbell, J. L. and Markesbery, W. R. (1998). Copper, iron and Zinc in Alzheimer's disease senile plaques. J Neurol Sci 158, 47-52.
[16] Frederickson, C. J. and Bush, A. I. (2001). Synaptically released zinc: physiological functions and pathological effects. Biometals 14, 353-66.
[17] Frederickson, C. J., Suh, S. W., Silva, D. and Thompson, R. B. (2000). Importance of zinc in the central nervous system: the zinc-containing neuron. J Nutr 130, 1471S-83S.
[18] Friedlich, A. L. et al. (2004). Neuronal zinc exchange with the blood vessel wall promotes cerebral amyloid angiopathy in an animal model of Alzheimer's disease. J Neurosci 24, 3453-9.
[19] Bush, A. I. (2003). Copper, zinc, and the metallobiology of Alzheimer disease. Alzheimer Dis Assoc Disord 17, 147-50.
[20] Maynard, C. J., Bush, A. I., Masters, C. L., Cappai, R. and Li, Q. X. (2005). Metals and amyloid-beta in Alzheimer's disease. Int J Exp Pathol 86, 147-59.
[21] Auld, D. S., Kar, S, and Quirion, R. (1998). Beta-amyloid peptides as direct cholinergic neuromodulators: a missing link? Trends Neurosci 21, 43-9.
[22] Kelly, J. F., Furukawa, K., Barger, S. W., Rengen, M. R., Mark, R. J., Blanc, E. M., Roth, G. S. and Mattson, M. P. (1996). Amyloid beta-peptide disrupts carbachol-induced muscarinic cholinergic signal transduction in cortical neurons. Proc Natl Acad Sci USA 93, 6753-8.
[23] Mijailovic, B., Mladenovic, T., Karadaglic, D., Ninkovic, M., Jovic, P. and Pavlovic, M. (1996). [Clinical and laboratory studies of cholinergic urticaria]. Vojnosanit Pregl 53, 497-501.
[24] Pedersen, W. A., Kloczewiak, M. A. and Blusztajn, J. K. (1996). Amyloid beta-protein reduces acetylcholine synthesis in a cell line derived from cholinergic neurons of the basal forebrain. Proc Natl Acad Sci USA 93, 8068-71.
[25] Wu, J., Kuo, Y. P., George, A. A., Xu, L., Hu, J. and Lukas, R. J. (2004). beta-Amyloid directly inhibits human alpha4beta2-nicotinic acetylcholine receptors heterologously expressed in human SH-EP1 cells. J Biol Chem 279, 37842-51.

[26] Coyle, J. and Kershaw, P. (2001). Galantamine, a cholinesterase inhibitor that allosterically modulates nicotinic receptors: effects on the course of Alzheimer's disease. Biol Psychiatry 49, 289-99.

[27] Maelicke, A., Samochocki, M., Jostock, R., Fehrenbacher, A., Ludwig, J., Albuquerque, E. X. and Zerlin, M. (2001). Allosteric sensitization of nicotinic receptors by galantamine, a new treatment strategy for Alzheimer's disease. Biol Psychiatry 49, 279-88.

[28] Newhouse, P. A., Potter, A., Kelton, M. and Corwin, J. (2001). Nicotinic treatment of Alzheimer's disease. Biol Psychiatry 49, 268-78.

[29] Wang, H. Y., Li, W., Benedetti, N. J. and Lee, D. H. (2003). Alpha 7 nicotinic acetylcholine receptors mediate beta-amyloid peptide-induced tau protein phosphorylation. J Biol Chem 278, 31547-53.

[30] Christensen, D. D. (2007). Changing the Course of Alzheimer's Disease: Anti-Amyloid Disease-Modifying Treatments on the Horizon. J Clin Psychiatry 9, 32-41.

[31] Gervais, F. et al. (2007). Targeting soluble Abeta peptide with Tramiprosate for the treatment of brain amyloidosis. Neurobiol Aging 28, 537-47.

[32] Velazquez, P., Cribbs, D. H., Poulos, T. L. and Tenner, A. J. (1997). Aspartate residue 7 in amyloid beta-protein is critical for classical complement pathway activation: implications for Alzheimer's disease pathogenesis. Nat Med 3, 77-9.

[33] Giulian, D. et al. (1998). The HHQK domain of beta-amyloid provides a structural basis for the immunopathology of Alzheimer's disease. J Biol Chem 273, 29719-26.

[34] Bronfman, F. C., Garrido, J., Alvarez, A., Morgan, C. and Inestrosa, N. C. (1996). Laminin inhibits amyloid-beta-peptide fibrillation. Neurosci Lett 218, 201-3.

[35] Castillo, G. M., Lukito, W., Peskind, E., Raskind, M., Kirschner, D. A., Yee, A. G. and Snow, A. D. (2000). Laminin inhibition of beta-amyloid protein (Abeta) fibrillogenesis and identification of an Abeta binding site localized to the globular domain repeats on the laminin a chain. J Neurosci Res 62, 451-62.

[36] Murtomaki, S., Risteli, J., Risteli, L., Koivisto, U. M., Johansson, S. and Liesi, P. (1992). Laminin and its neurite outgrowth-promoting domain in the brain in Alzheimer's disease and Down's syndrome patients. J Neurosci Res 32, 261-73.

[37] Caplan, M. R., Schwartzfarb, E. M., Zhang, S., Kamm, R. D. and Lauffenburger, D. A. (2002). Control of self-assembling oligopeptide matrix formation through systematic variation of amino acid sequence. Biomaterials 23, 219-27.

[38] Zhang, S. (2002). Emerging biological materials through molecular self-assembly. Biotechnol Adv 20, 321-39.

[39] Buneeva, O. Proteomics 2010, 10, 23-37.

---

The invention claimed is:

1. A peptide compound selected from the group consisting of HADD (SEQ. ID. NO. 1), KADD (SEQ. ID. NO. 3), DDAK (SEQ. ID. NO. 4), RADD (SEQ. ID. NO. 5), DDAR (SEQ. ID. NO. 6), KAED (SEQ. ID. NO. 9), DEAK (SEQ. ID. NO. 10), RAED (SEQ. ID. NO. 11), DEAR (SEQ. ID. NO. 12), HADE (SEQ. ID. NO. 13), EDAH (SEQ. ID. NO. 14), KADE (SEQ. ID. NO. 15), EDAK (SEQ. ID. NO. 16), RADE (SEQ. ID. NO. 17), EDAR (SEQ. ID. NO. 18), HAEE (SEQ. ID. NO. 19), EEAH (SEQ. ID. NO. 20), KAEE (SEQ. ID. NO. 21), EEAK (SEQ. ID. NO. 22), RAEE (SEQ. ID. NO. 23), and EEAR (SEQ. ID. NO. 24);
   wherein the N-terminus primary amine function of the peptide compound is substituted with a protective group; and
   wherein the hydroxyl function of the C-terminus carboxyl group of the peptide compound is substituted with a protective group.

2. The peptide compound according to claim 1,
   wherein the peptide compound has a degree of purity of at least 98%;
   wherein the peptide compound is in a form of a natural L isomer;
   wherein the N-terminus primary amine function of the peptide compound is substituted with a protective group; and
   wherein the hydroxyl function of the C-terminus carboxyl group of the peptide compound is substituted with a protective group.

3. The peptide compound according to claim 1, wherein the peptide compound is HAEE (SEQ. ID. NO. 19) or RADD (SEQ. ID. NO. 5) acetylated at the N-terminus end and amidated at the C-terminus end.

4. The peptide compound according to claim 1, wherein the peptide compound is in a form of a natural L isomer.

5. The peptide compound according to claim 1, wherein the peptide compound is DDAK (SEQ. ID. NO. 4), RADD (SEQ. ID. NO. 5), or DDAR (SEQ. ID. NO. 6) in a form of a natural L isomer.

6. The peptide compound according to claim 1, wherein the protective groups associated with the N-terminus primary amine function of the peptide compound and the hydroxyl function of the C-terminus carboxyl group of the peptide compound, are protective groups compatible with pharmaceutical use in vivo.

7. The peptide compound according to claim 1,
   wherein the hydroxyl function of the C-terminus carboxyl group of the peptide compound is substituted with a protective group selected from the group consisting of —$NH_2$, —NHR, and —NRR; wherein R is a $C_1$-$C_4$ alkyl or —O—$R_1$, wherein $R_1$ is a $C_1$-$C_4$ alkyl or an alkylamine.

8. The peptide compound according to claim 1,
   wherein the N-terminus amine function of the peptide compound is substituted with a protective group selected from the group consisting of a formyl group (HCO—) and an acetyl group ($CH_2CO$—).

9. The peptide compound according to claim 1, wherein the peptide compound is selected from the group consisting of HADD (SEQ. ID. NO. 1), KADD (SEQ. ID. NO. 3), DDAK (SEQ. ID. NO. 4), RADD (SEQ. ID. NO. 5), KAED (SEQ. ID. NO. 9), DEAR (SEQ. ID. NO. 12), HADE (SEQ. ID. NO. 13), KADE (SEQ. ID. NO. 15), RADE (SEQ. ID. NO. 17),), EDAR (SEQ. ID. NO. 18), HAEE (SEQ. ID. NO. 19), EEAH (SEQ. ID. NO. 20), KAEE (SEQ. ID. NO. 21), EEAK (SEQ. ID. NO. 22), RAEE (SEQ. ID. NO. 23), and EEAR (SEQ. ID. NO. 24).

10. The peptide compound according to claim 9, wherein the peptide compound is selected from the group consisting of HADD (SEQ. ID. NO. 1), DDAK (SEQ. ID. NO. 4), RADD (SEQ. ID. NO. 5), KAED (SEQ. ID. NO. 9), DEAR (SEQ. ID. NO. 12), KADE (SEQ. ID. NO. 15), HAEE (SEQ. ID. NO. 19), and RAEE (SEQ. ID. NO. 23), and wherein DDAK (SEQ. ID. NO. 4) and DDAR (SEQ. ID. NO. 6) are in a form of a natural L isomer.

11. The peptide compound according to claim 9, wherein the peptide compound is HAEE (SEQ. ID. NO. 19) or RADD (SEQ. ID. NO. 5).

12. The peptide compound according to claim 9, wherein the peptide compound is DDAK (SEQ. ID. NO. 4) or DDAR (SEQ. ID. NO. 6) in a form of a natural L isomer.

13. A composition comprising an active substance comprising:
- a peptide compound according to claim 1; and
- a pharmaceutically acceptable carrier.

14. A pharmaceutical composition comprising the composition according to claim 13, wherein the pharmaceutically acceptable carrier is suitable for use for parenteral, transcutaneous, or transmucosal administration.

15. The pharmaceutical composition according to claim 14, wherein the pharmaceutically acceptable carrier is suitable for use for intravascular, intramuscular, subcutaneous, intraspinal or cerebrospinal administration.

16. A method of treatment of a disease related to the formation of amyloid-β plaques, the method comprising administering to a patient in need thereof a pharmaceutical composition according to claim 14.

17. The method according to claim 16, wherein the peptide compound is HAEE (SEQ. ID. NO. 19) or RADD (SEQ. ID. NO. 5).

18. The method according to claim 16, wherein the disease is Alzheimer's disease.

19. A method according to claim 18, wherein the peptide compound is HAEE (SEQ. ID. NO. 19) or RADD (SEQ. ID. NO. 5).

20. A method for reducing binding of Zn(II) ions to an amyloid-β peptide, the method comprising:
binding a peptide compound to the amyloid-β peptide;
wherein the peptide compound is selected from the group consisting of HADD (SEQ. ID. NO. 1), KADD (SEQ. ID. NO. 3), DDAK (SEQ. ID. NO. 4), RADD (SEQ. ID. NO. 5), DDAR (SEQ. ID. NO. 6), KAED (SEQ. ID. NO. 9), DEAK (SEQ. ID. NO. 10), RAED (SEQ. ID. NO. 11), DEAR (SEQ. ID. NO. 12), HADE (SEQ. ID. NO. 13), EDAH (SEQ. ID. NO. 14), KADE (SEQ. ID. NO. 15), EDAK (SEQ. ID. NO. 16), RADE (SEQ. ID. NO. 17), EDAR (SEQ. ID. NO. 18), HAEE (SEQ. ID. NO. 19), EEAH (SEQ. ID. NO. 20), KAEE (SEQ. ID. NO. 21), EEAK (SEQ. ID. NO. 22), RAEE (SEQ. ID. NO. 23), and EEAR (SEQ. ID. NO. 24);

wherein the N-terminus primary amine function of the peptide compound is either free or substituted with a protective group; and wherein the hydroxyl function of the C-terminus carboxyl group of the peptide compound being either free or substituted with a protective group.

21. The method according to claim 20, wherein the peptide compound is HAEE (SEQ. ID. NO. 19) or RADD (SEQ. ID. NO. 5).

22. A method for reducing polymerization or aggregation of an amyloid-β peptide in the presence of Zn(II) ions, the method comprising:
binding a peptide compound to the amyloid-β peptide;
wherein the peptide compound is selected from the group consisting of HADD (SEQ. ID. NO. 1), KADD (SEQ. ID. NO. 3), DDAK (SEQ. ID. NO. 4), RADD (SEQ. ID. NO. 5), DDAR (SEQ. ID. NO. 6), KAED (SEQ. ID. NO. 9), DEAK (SEQ. ID. NO. 10), RAED (SEQ. ID. NO. 11), DEAR (SEQ. ID. NO. 12), HADE (SEQ. ID. NO. 13), EDAH (SEQ. ID. NO. 14), KADE (SEQ. ID. NO. 15), EDAK (SEQ. ID. NO. 16), RADE (SEQ. ID. NO. 17), EDAR (SEQ. ID. NO. 18), HAEE (SEQ. ID. NO. 19), EEAH (SEQ. ID. NO. 20), KAEE (SEQ. ID. NO. 21), EEAK (SEQ. ID. NO. 22), RAEE (SEQ. ID. NO. 23), and EEAR (SEQ. ID. NO. 24);

wherein the N-terminus primary amine function of the peptide compound is either free or substituted with a protective group; and wherein the hydroxyl function of the C-terminus carboxyl group of the peptide compound being either free or substituted with a protective group.

23. The method according to claim 22, wherein the peptide compound is HAEE (SEQ. ID. NO. 19) or RADD (SEQ. ID. NO. 5).

* * * * *